United States Patent [19]

Furutachi

[11] 4,199,361

[45] Apr. 22, 1980

[54] COLOR PHOTOGRAPHIC LIGHT-SENSITIVE ELEMENT

[75] Inventor: Nobuo Furutachi, Minami-ashigara, Japan

[73] Assignee: Fuji Photo Film Co., Ltd., Minami-ashigara, Japan

[21] Appl. No.: 950,118

[22] Filed: Oct. 10, 1978

[30] Foreign Application Priority Data

Oct. 14, 1977 [JP] Japan .................................. 52/122500

[51] Int. Cl.² ............................................... G03C 1/40
[52] U.S. Cl. .................................... 430/508; 548/374; 430/554; 430/570
[58] Field of Search ................... 96/100, 56.5, 74, 120; 260/310 A

[56] References Cited

U.S. PATENT DOCUMENTS

| 3,798,234 | 3/1974 | Meier et al. ............................ 96/100 |
| 3,907,571 | 9/1975 | Arai et al. ............................. 96/100 |
| 3,935,015 | 1/1976 | Arai et al. ............................. 96/100 |
| 3,960,571 | 6/1976 | Okumura et al. ....................... 96/100 |
| 4,062,683 | 12/1977 | Monbaliu et al. ...................... 96/100 |

*Primary Examiner*—Won H. Louie, Jr.
*Attorney, Agent, or Firm*—Sughrue, Rothwell, Mion, Zinn and Macpeak

[57] ABSTRACT

A color photographic light-sensitive element comprising a support having thereon a silver halide emulsion layer containing therein a 3-anilino-5-pyrazolone magenta color-forming coupler represented by the following general formula (I):

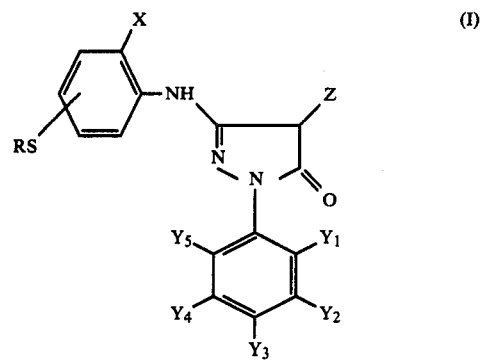

wherein R represents an aliphatic hydrocarbon group having up to about 35 carbon atoms, a heterocyclic group having up to about 22 carbon atoms or an aromatic group having up to about 22 carbon atoms; X represents a halogen atom or an alkoxy group having up to about 22 carbon atoms; Z represents a hydrogen atom or a coupling off group; and $Y_1$, $Y_2$, $Y_3$, $Y_4$ and $Y_5$, which may be the same or different, each represents a hydrogen atom, a halogen atom, a cyano group, an alkyl group having 1 to 5 carbon atoms, a trifluoromethyl group, an alkoxy group having 1 to 5 carbon atoms, an acylamino group having 1 to 30 carbon atoms, an alkylsulfonyl group having 2 to 30 carbon atoms or a sulfonamido group having 1 to 30 carbon atoms and the RS group is present at the 4- or 5-position of the anilino group. The magenta color-forming coupler prevents yellow staining at the unexposed area after color development processing particularly arising due to irradiation of light.

11 Claims, No Drawings

COLOR PHOTOGRAPHIC LIGHT-SENSITIVE ELEMENT

BACKGROUND OF THE INVENTION

1. Field of the Invention

The present invention relates to a silver halide photographic light-sensitive element containing a novel magenta color forming coupler.

2. Description of the Prior Art

After exposing a silver halide photographic light-sensitive element to light, the element is developed with an aromatic primary amine developing agent. The developing agent is oxidized by color development and reacts with a coupler to form a dye, thus, a color image being formed. In this system, a subtractive method is generally used for color reproduction, in which blue, green and red colors are reproduced by forming yellow, magenta and cyan color images which are in complimentary relation thereto, respectively. In general, acrylacetamide or dibenzoylmethane type couplers are employed for forming yellow color images, pyrazolone, cyanoacetyl or indazolone type couplers are used for forming magenta color images, and phenol type couplers, for example, phenols and naphthols, are utilized for forming cyan color images.

To produce color photographs, couplers which form dyes are incorporated into a developer or are present in a light-sensitive photographic emulsion layer(s).

A variety of 5-pyrazolone type couplers for forming magenta color images are known. Known substituents at the 3-position of the 5-pyrazolone ring include an alkyl group, an aryl group, the alkoxy groups as described in U.S. Pat. No. 2,439,098, the acylamino groups as described in U.S. Pat. Nos. 2,369,489 and 2,600,788, and the ureido groups as described in U.S. Pat. No. 3,558,319 and an anilino group. 3-Anilino-5-pyrazolone type couplers have often been described in the art since U.S. Pat. No. 2,311,081 (U.S. Pat. No. Re. 22,329) was issued and several improvements therein have been proposed. British Patent No. 956,261 discloses that azomethine dyes obtained from derivatives in which the ortho position of the anilino group is substituted with an alkoxy group or a halogen atom have advantageous spectral absorption properties for color photography in that undesired absorption in the red light region is particularly low.

Specific examples of diffusion resistant couplers which belong to this type and are capable of being incorporated into photographic emulsions are described in U.S. Pat. Nos. 3,930,861, 3,907,571, 3,928,044 and 3,935,015, etc. For example, the couplers described in U.S. Pat. No. 3,935,015 are well known and are 3-(acylaminoanilino)-5-pyrazolones represented by the formula (M) below:

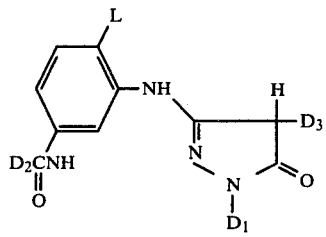

(M)

wherein $D_1$ represents an aryl group or a heterocyclic group, $D_2$ represents a straight chain, branched chain or cyclic alkyl group having 7 to 23 carbon atoms, $D_3$ represents a splitting off group, and L represents an alkoxy group having 1 to 18 carbon atoms or a halogen atom.

These couplers have the characteristics that the undesired absorption of magenta azomethine dyes obtained upon color formation using the same in the red light region is low, the cut-off of the main absorption is good at the longer wavelength side, and magenta color images having a high color density are obtained because the coupling speed is high, and, further, the solubility in organic solvents having a high boiling point is improved so that, after dissolving these couplers in organic solvents, the couplers are emulsion-dispersed in an aqueous medium in the form of fine colloidal particles and then added to emulsions. However, these couplers have the disadvantages that the degree of yellow staining at the unexposed portion after color development processing is high and this degree of yellow staining is increased upon irradiation with light, and, further, have the disadvantages that color fading of the magenta color images obtained upon color development using these compounds occurs to a marked degree upon irradiation with light and the color balance required for color photography is damaged by exposure to light. These disadvantages become fatal defects for color light-sensitive elements, such as color printing papers and the like. Thus, improved couplers which do not have these disadvantages have been strongly desired.

SUMMARY OF THE INVENTION

A first object of the present invention is to provide a coupler with which the formation of yellow stain at the unexposed areas of a color photographic light-sensitive element after color development processing is minimized, and, further, with which yellow stain does not occur nor does a fresh yellow stain upon irradiation with light occur.

A second object of the present invention is to provide a coupler having the property that color images formed therefrom fade with difficulty even if the magenta color images obtained after color development are irradiated with light.

A third object of the present invention is to provide a light-sensitive element which can be used to reproduce a clear color by the subtractive method.

A fourth object of the present invention is to provide a light-sensitive element which is suitable for a simple development processing without stabilizing processing with formaldehyde or the like being required.

A fifth object of the present invention is to provide a novel coupler which has a high color formation rate and provides magenta color images having a high density.

A sixth object of the present invention is to provide a coupler which has excellent solubility in an organic solvent and is suitable for use in a method which comprises emulsion-dispersing the coupler in an aqueous medium in the form of fine colloidal particles and then incorporating the dispersion into an emulsion.

These and other objects of the present invention will become more apparent from the detailed description of the invention and the examples given hereinbelow.

These objects are effectively achieved by a color photographic light-sensitive element containing in a silver halide photographic emulsion layer(s) thereof, as a magenta color image-forming coupler, a 3-anilino-5- pyrazolone coupler wherein the anilino group thereof is substituted with a halogen atom or an alkoxy group at the 2-position of the anilino group and with an aliphaticthio group, an aromaticthio group or a heterocyclic thio group at the 4- or 5-position of the anilino group and also a aryl group is present at the 1-position of the pyrazolone nucleus. Further, the 4-position of the pyrazolone nucleus may also be a hydrogen atom, or may be substituted with a coupling off group.

DETAILED DESCRIPTION OF THE INVENTION

The term "coupling off group" as used herein has the same meaning as generally used in the color-forming coupler field and refers to a group which is eliminated by the oxidation product of an aromatic primary amine developing agent on coupling.

Couplers which are useful for the present invention include compounds represented by the following general formula (I):

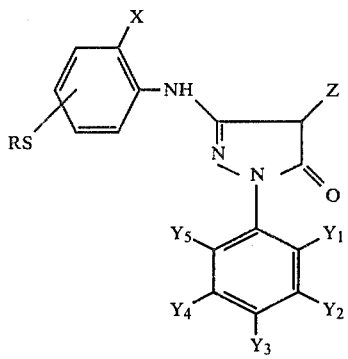

wherein R represents an aliphatic hydrocarbon group having up to about 35 carbon atoms (including, for example, an alkyl group, an alkenyl group, a cycloalkyl group, a cycloalkenyl group, an aralkyl group, etc.), a heterocyclic group having 5 to 22 carbon atoms (for example, 5- or 6-membered heterocyclic rings), or an aromatic group having up to 22 carbon atoms; X represents a halogen atom or an alkoxy group having up to 22 carbon atoms; Z represents a hydrogen atom or a coupling off group; and $Y_1$, $Y_2$, $Y_3$, $Y_4$ and $Y_5$, which may be the same or different, each represents a hydrogen atom, a halogen atom, a cyano group, an alkyl group having 1 to 5 carbon atoms, a trifluoromethyl group, an alkoxy group having 1 to 5 carbon atoms, an acylamino group having 1 to 30 carbon atoms, an alkylsulfonyl group having 1 to 30 carbon atoms, an alkoxycarbonyl group having 2 to 30 carbon atoms or a sulfonamido group having 1 to 30 carbon atoms, and RS group is present at the 4- or 5-position of the anilino group.

R, X, Z, $Y_1$, $Y_2$, $Y_3$, $Y_4$ and $Y_5$ in the general formula (I) above are described in detail hereinbelow.

In the general formula (I), R can be a straight chain, branched chain or cyclic aliphatic group having up to 35 carbon atoms and, preferably, represents an alkyl group (for example, straight chain or branched chain, such as a methyl, ethyl, heptyl, tetradecyl, hexadecyl, octadecyl, dodecyl, etc., group), an alkenyl group (for example, straight chain or branched chain, such as an allyl, etc., group), a cycloalkyl group (including a bridged cycloalkyl group, for example, a cyclopentyl, cyclohexyl, norbornyl, etc., group), an aralkyl group (e.g., a benzyl, phenethyl, etc., group), a cycloalkenyl group (e.g., a cyclopentenyl, cyclohexenyl, etc., group), each having up to 22 carbon atoms; which can be substituted with one or more substituents selected from halogen atoms (e.g., chlorine and bromine) and nitro, cyano, aryl (e.g., phenyl, naphthyl, etc.), alkoxy (e.g., methoxy, ethoxy, etc.), aryloxy (e.g., phenyloxy, naphthyloxy, etc.), carboxy, alkylcarbonyl (e.g., acetyl, tetradecanoyl, etc.), arylcarbonyl (e.g., benzoyl, etc.), alkoxycarbonyl (e.g., methoxycarbonyl, benzyloxycarbonyl, etc.), aryloxycarbonyl (e.g., phenyloxycarbonyl, p-tolyloxycarbonyl, etc.), sulfo, acyloxy (e.g., acetyloxy, tetradecanoyloxy, etc.), sulfamoyl (e.g., N-ethylsulfamoyl, N-octadecylsulfamoyl, etc.), carbamoyl (e.g., N-ethylcarbamoyl, N-methyl-N-dodecylcarbamoyl, etc.), acylamino (e.g., acetamido, benzamido, etc.), diacylamino (e.g., succinimido, hydantoinyl, etc.), ureido (e.g., methylureido, phenylureido, etc.), thioureido (e.g., phenylthioureido, etc.), urethane (e.g., tetradecyloxycarbonylamino, phenoxycarbonylamino, etc.), thiourethane (e.g., methoxythiocarbonylamino, etc.), sulfonamido (e.g., methylsulfonamido, etc.), heterocyclic (e.g., furyl, pyridyl, thienyl, etc.), arylsulfonyloxy (e.g., phenylsulfonyloxy, etc.), alkylsulfonyloxy (e.g., methylsulfonyloxy, dodecylsulfonyloxy, etc.), arylsulfonyl (e.g., phenylsulfonyl, etc.), alkylsulfonyl (e.g., methylsulfonyl, butylsulfonyl, etc.), alkylsulfinyl (e.g., methylsulfinyl, octadecylsulfinyl, etc.), arylsulfinyl (e.g., phenylsulfinyl, etc.), alkylamino (e.g., methylamino, dodecylamino, etc.), dialkylamino (e.g., N,N-diethylamino, N-methyl-N-dodecylamino, etc.), anilino (e.g., phenylamino, p-methoxyphenylamino, etc.), N-arylanilino (e.g., N-phenylanilino, N-phenyl-N-(4-methoxyphenyl)amino, etc.), N-alkylanilino (e.g., N-methylanilino, N-butylanilino, etc.), N-acylanilino (e.g., N-acetylanilino, N-trichloroacetylanilino, etc.), hydroxy and mercapto groups. Where R is an alkyl group substituted with a fluorine atom, R can also be a perfluoroalkyl group.

Further, R represents a monocyclic or bicyclic aromatic group having up to 22 carbon atoms such as an aryl group (for example, a phenyl, α- or β-naphthyl, etc., group) and a monocyclic or bicyclic aryl group substituted with one or more substituents. Suitable substituents can be an aliphatic hydrocarbon group, as described above for R.

Furthermore, R represents a heterocyclic group having up to 22 carbon atoms (for example, a 5- or 6-membered heterocyclic ring or condensed heterocyclic ring group containing, as a hetero atom, a nitrogen atom, an oxygen atom and/or a sulfur atom, e.g., a pyridyl, quinolyl, furyl, benzothiazolyl, oxazolyl, imidazolyl, naphthoxazolyl, etc., group) or a heterocyclic group having up to 22 carbon atoms which is substituted with one or more of the substituents as described above for the aryl group for R.

In the general formula (I), X represents a halogen atom (for example, chlorine, bromine, etc.) or an alkoxy group having 1 to 22 carbon atoms (for example, a methoxy, ethoxy, heptoxy, tetradecyloxy, β-chloroethoxy, hexadecyloxy, octadecyloxy, dodecyloxy, allyloxy, benzyloxy, phenethyloxy, etc., group). Such alkoxy groups can be substituted with one or more substituents selected from halogen atoms and nitro, cyano, alkoxy (for example, methoxy, ethoxy, etc.), aryloxy (for example, phenyloxy, naphthyloxy, etc.), alkylcarbonyl (for example, acetyl, tetradecanoyl, etc.), alkoxycarbonyl (for example, methoxycarbonyl, benzyloxycarbonyl, etc.), acylamino (for example, acetylamino, benzamido, etc.), sulfonamido (for example, methylsulfonamido, p-toluenesulfonamido, etc.), hydroxy and mercapto groups. Where X is an alkoxy group substituted with a fluorine atom, X can be a perfluoroalkoxy group.

In the general formula (I), Z represents a hydrogen atom and, in addition thereto, a coupling-off group. Suitable coupling-off groups represented by Z are, for instance, a thiocyano group, an acyloxy group (e.g., an acetoxy, dodecanoyloxy, octadecanoyloxy, 3-pentadecylphenoxyacetoxy, benzoyloxy, β-naphthoyloxy, 3-[γ-(2,4-di-tert-amylphenoxy)-butyramido]benzoyloxy, etc., group), an aryloxy group (e.g., a phenoxy, p-chlorophenoxy, p-nitrophenoxy, naphthoxy, etc., group), an alkoxy group (e.g., methoxy, ethoxy, β-methylsulfonamidoethoxy, etc.), a halogen atom (e.g., a chlorine, fluorine, etc., atom), an arylazo group (e.g., a phenylazo, 2-methyl-4-hydroxyphenylazo, naphthylazo, etc., group), an aryltriazolyl group (e.g., a 1-benzotriazolyl, 2-benzotriazolyl, 2-naphthotriazolyl, etc., group), an alkylthio group (e.g., octylthio, dodecylthio, etc.), an arylthio group (e.g., a phenylthio, naphthylthio, etc., group), an aralkoxycarbonyloxy group (e.g., a benzyloxycarbonyloxy, etc., group), an alkoxycarbonyloxy group (e.g., ethoxycarbonyloxy, benzyloxycarbonyloxy, etc.), an aryloxycarbonyloxy group (e.g., phenoxycarbonyloxy, etc.), a heterocyclic thio group (e.g., a 2-benzothiazolylthio, 1-phenyl-5-tetrazolylthio, 2-benzoxazolylthio, 2-benzimidazolylthio, 5-phenyl-1,3,4-oxadiazolyl-2-thio, etc., group), a cycloalkylthio group (e.g., a cyclohexylthio, etc., group), a cycloalkoxy group (e.g., a cyclohexyloxy, etc., group), an imido group (e.g., a phthalimido, succinimido, 5,5-dimethyl-3-hydantoinyl, 5,5-dimethyl-3-oxazolidinyl, etc., group), an imidazolyl group (e.g., a 1-imidazolyl, 2-methyl-1-imidazolyl, 1-benzimidazolyl, etc., group), a triazolyl group (e.g., a 3,5-diethyl-1,2,4-triazolyl, etc., group), an acylamino group (e.g., a benzamido, acetamido, etc., group), a sulfonamido group (e.g., a benzenesulfonamido, methylsulfonamido, etc., group), a cycloamino group (e.g., a piperidino, morpholino, etc., group), etc.

In the general formula (I), a phenyl group substituted with $Y_1$, $Y_2$, $Y_3$, $Y_4$ and $Y_5$ and present at 1-position of pyrazolone ring (for example, a phenyl, 2-chlorophenyl, 4-chlorophenyl, 2,5-dichlorophenyl, 2,6-dichlorophenyl, 2,4,6-trichlorophenyl, 2-bromophenyl, 3,5-dibromophenyl, 2-cyanophenyl, 2,6-dichloro-4-cyanophenyl, 4-cyanophenyl, 4-methylphenyl, 2,6-dimethylphenyl, 4-butylphenyl, 2-trifluoromethylphenyl, 2-ethoxyphenyl, N-methylbenzamidophenyl, phenyl-N-methylsulfonamidophenyl, 2,6-dichloro-4-[α-(2,4-di-tert-amylphenoxy)butanamido]phenyl, 2,3,4,5,6-pentafluorophenyl, 2,3,4,5,6-pentachlorophenyl, 2-chloro-5-cyanophenyl, 5-chloro-2-methylphenyl, 2,6-dichloro-4-methylphenyl, 2,4-dichloro-6-methylphenyl, 2-chloro-4,6-dimethylphenyl, 2,6-dichloro-4-methoxyphenyl, 2,6-dichloro-4-methoxycarbonylphenyl, 2,6-dichloro-4-methylsulfonylphenyl, etc., group.

The magenta color-forming couplers represented by the general formula (I) above are novel couplers.

Of these magenta color-forming couplers employed in the present invention, particularly preferred couplers are those represented by the general formula (II) below.

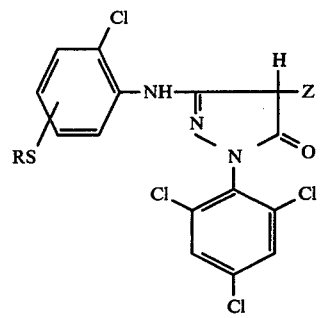

(II)

wherein R and Z have the same meanings as defined in the general formula (I), and the RS-group is preferably present at the 4- or 5-position of the anilino ring.

The couplers represented by the general formula (II) are particularly preferred because the spectral absorption curve of the magenta color images obtained especially upon color development is sharp, a second absorption zone which is characteristic of conventional pyrazolone type magenta couplers is small, and the melting point thereof is low and, furhter, solubility in an organic solvent having a high boiling point is high. Further, couplers in which the RS-group is directly bonded to the anilino group as a ballast group are particularly advantageous since they minimize the formation of yellow stain at the unexposed areas of a color photographic element after color development processing, and, further, they do not increase the yellow stain nor cause fresh yellow stain upon irradiation with light, as shown in the Examples hereinafter.

5-Pyrazolone type magenta couplers having a sulfide group in a ballast group are known, for example, as described in German Patent Application (OLS) No. 2,301,705, U.S. Pat. No. 3,580,721, Belgian Patent No. 656,604, *Research Disclosure*, No. 13432 (1975), etc. However, these compounds are structurally different from the couplers according to the present invention in which a ballast group is directly bonded to the anilino group through a sulfur atom, as described in greater detail below.

The couplers described in German Patent Application (OLS) No. 2,301,705, and U.S. Pat. No. 3,580,721, in which a sulfide bond is present in the terminal portion of a ballast group of the pyrazolone, are completely different in structure from the couplers of the present invention in which a sulfur atom is directly bonded to the anilino group. Further, due to the presence of the sulfide bond directly on the anilino group, when their photographic properties are compared, the couplers of the present invention are superior to the known couplers described above in view of the difference in hue of the color images obtained by color development processing, and, particularly, the small amount of fading of the color images formed on irradiation with light and the small amount of yellow stain at the unexposed areas after color development processing and the small degree that the yellow stain is increased upon irradiation with light.

The couplers in which a sulfide is bonded at the p-position of a phenyl group which is bonded to the 1-position of the pyrazolone ring as described in *Research Disclosure*, No. 13432 (1975) are also completely different from the couplers of the present invention in structure. When the photographic properties are compared, due to the presence of the sulfide bond directly on the anilino group, the couplers of the present invention are superior to the couplers described above in the spectral absorption characteristics of the color images formed upon color development processing and the fading properties upon irradiation with light.

As described above, the couplers of the present invention have various advantages in comparison with known couplers having a sulfide bond in that their chemical structures are novel, in that their photographic properties are superior, in that they have a high solubility to a high boiling point organic solvent, in that the spectral absorption characteristics of the color images formed on color development processing are excellent, in that the stability of the color images is excellent, in that yellow stain at the unexposed areas is low, and the like.

Specific examples of magenta color forming couplers which can be employed in the present invention are shown below, but the present invention is not to be construed as being limited thereto.

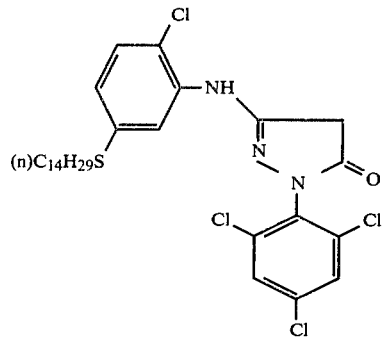

(1)

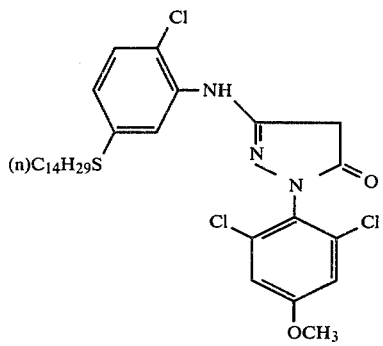

(2)

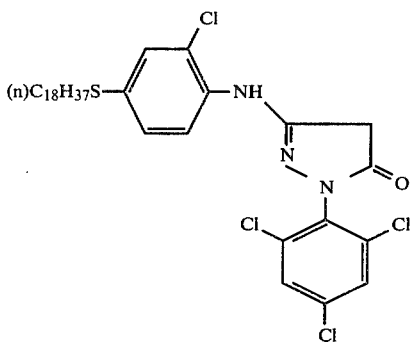

(3)

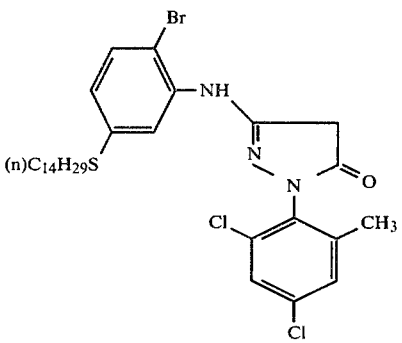

(4)

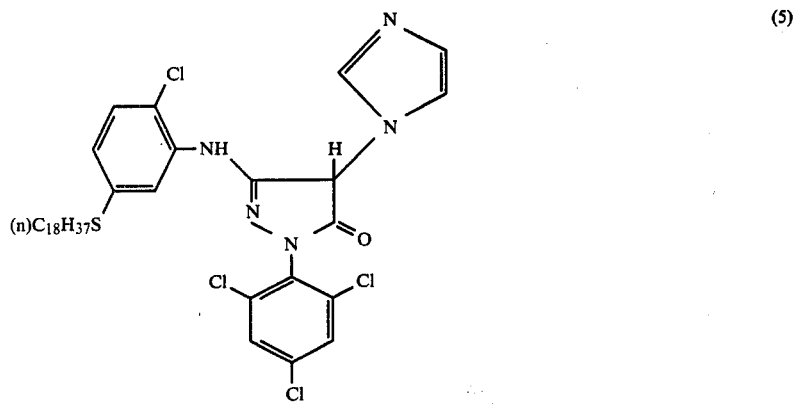
(5)
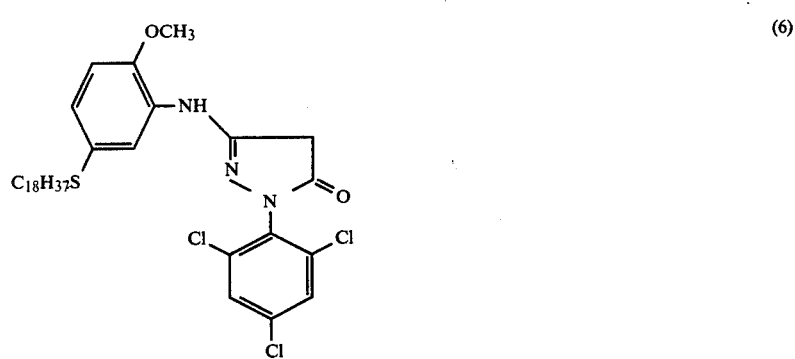
(6)
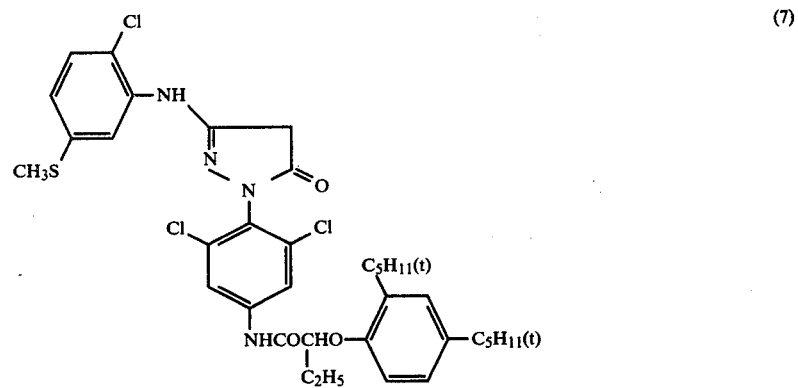
(7)
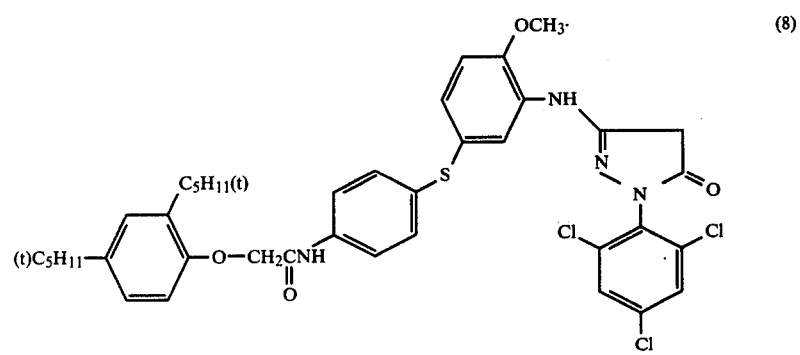
(8)

-continued
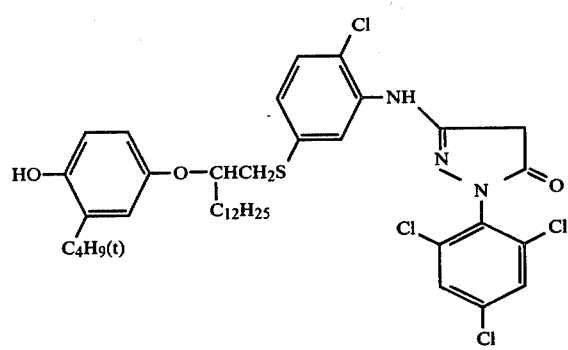 (9)
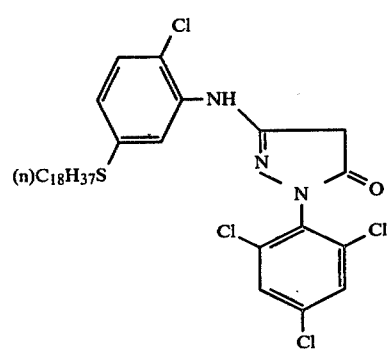 (10)
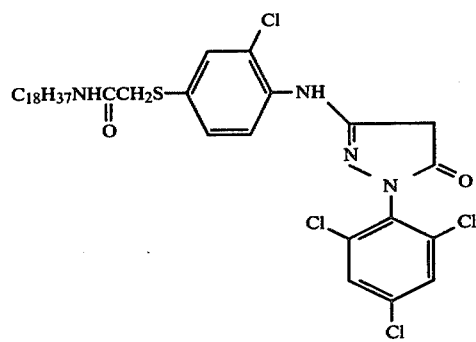 (11)
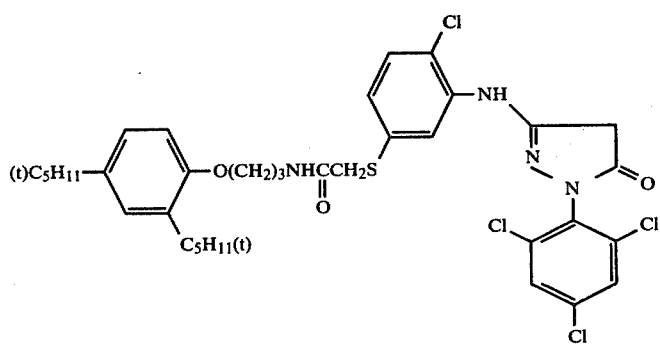 (12)

-continued
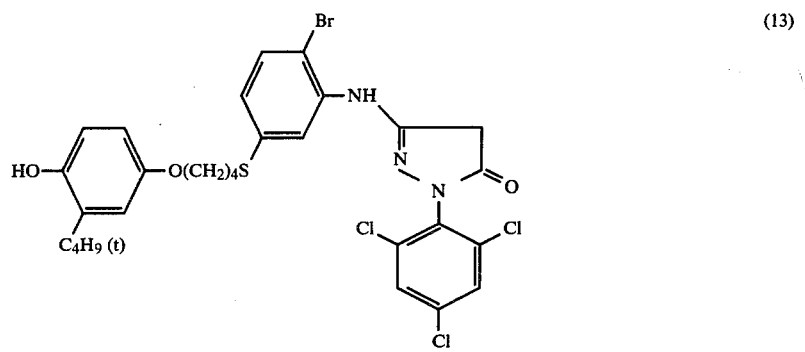
(13)
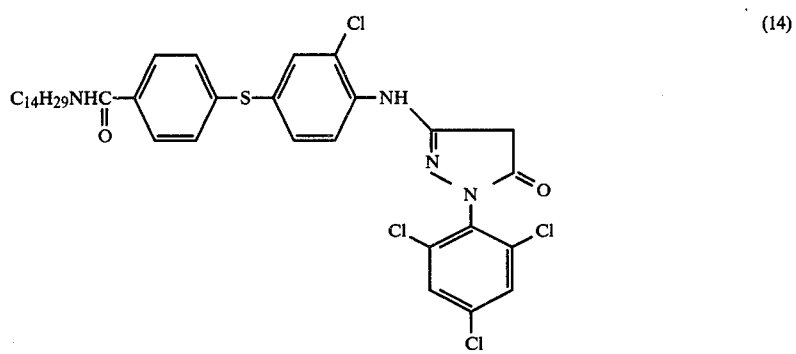
(14)
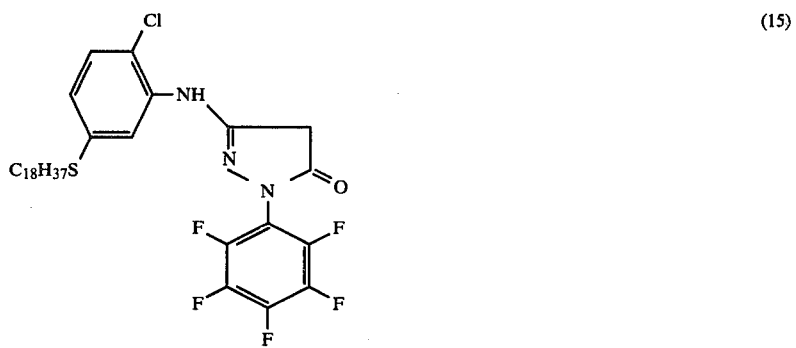
(15)
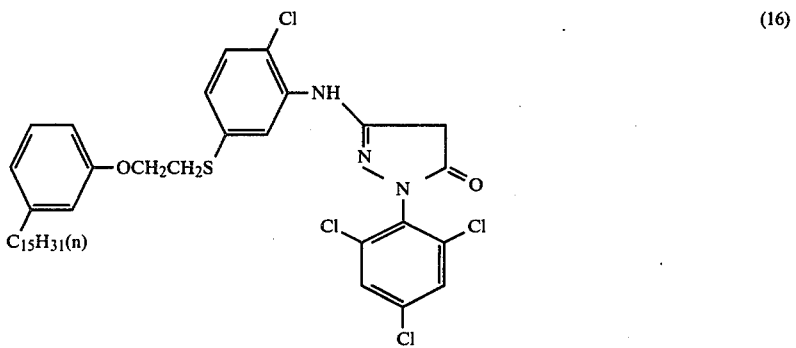
(16)

-continued
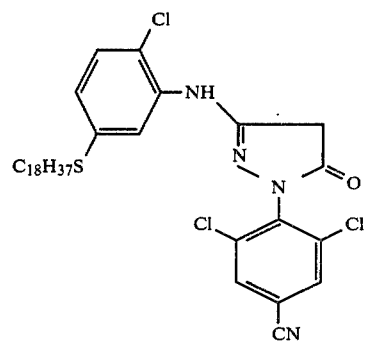
(17)
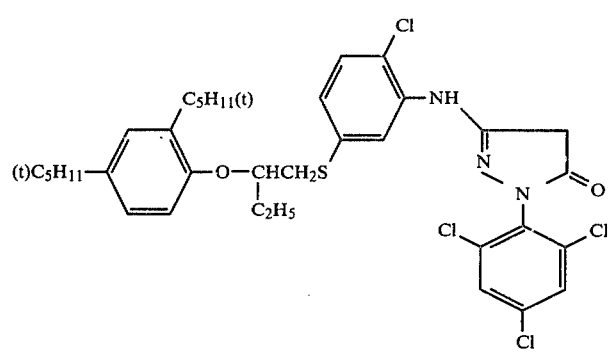
(18)
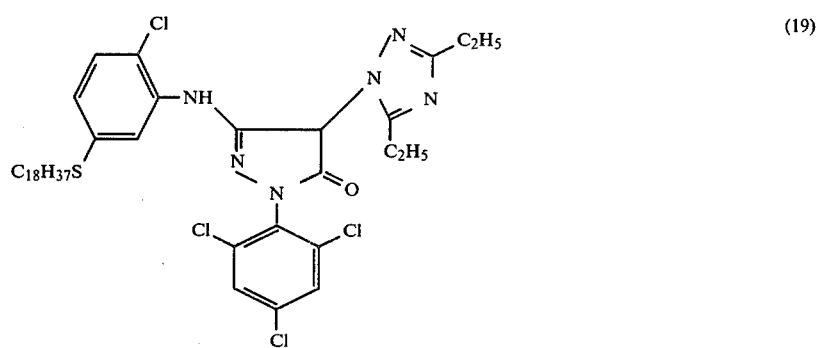
(19)
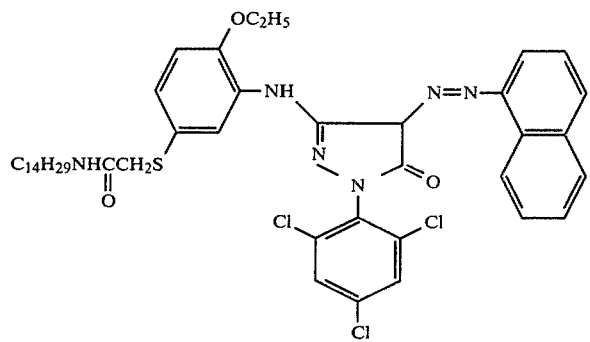
(20)

-continued
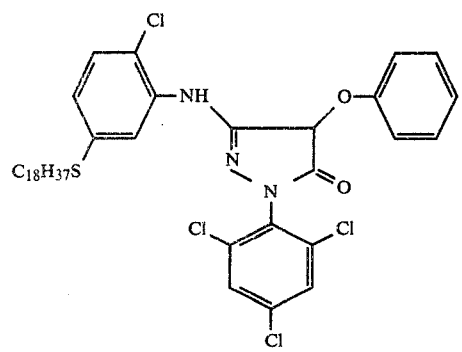
(21)
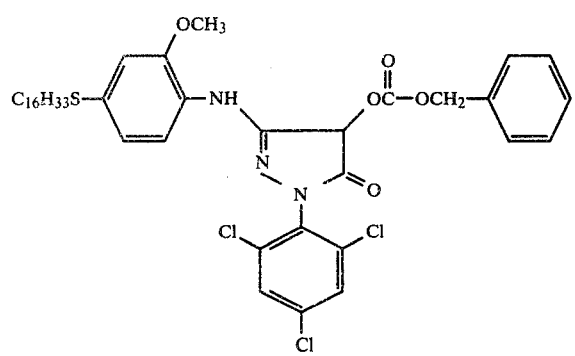
(22)
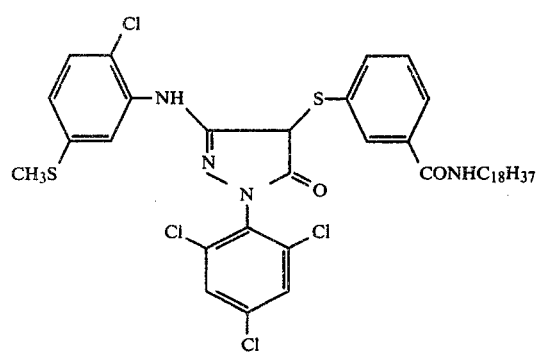
(23)
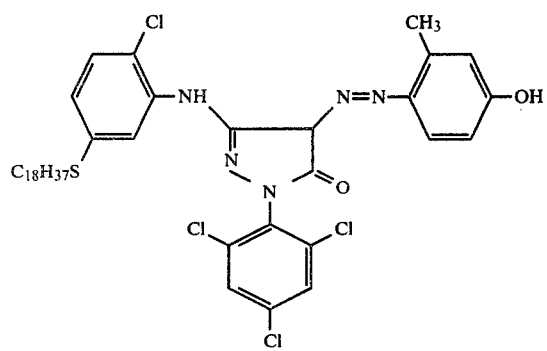
(24)

-continued
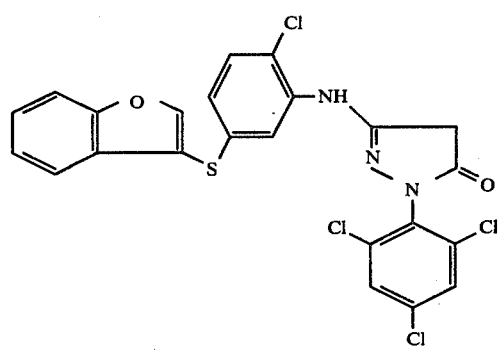 (25)
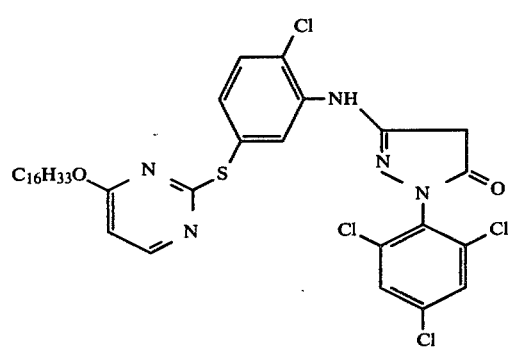 (26)
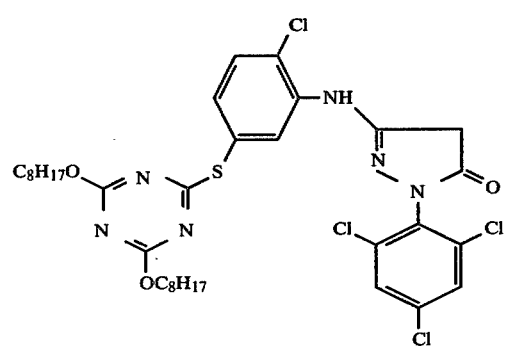 (27)
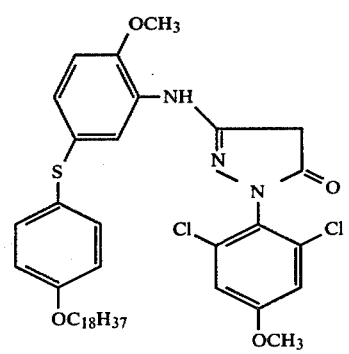 (28)

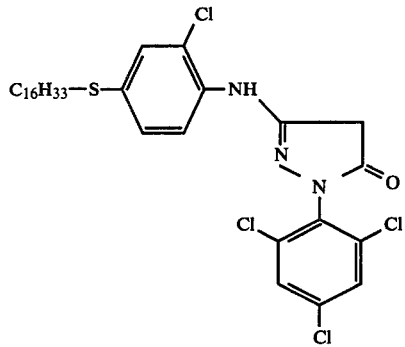
(29)

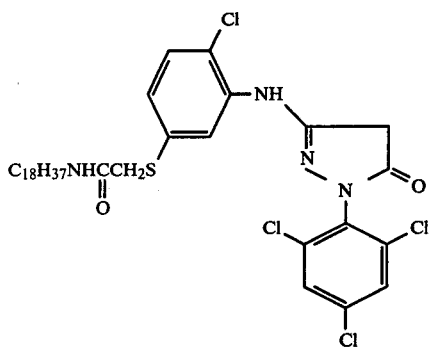
(30)

The magenta color-forming coupler of the present invention can be generally synthesized along the lines schematically shown below.

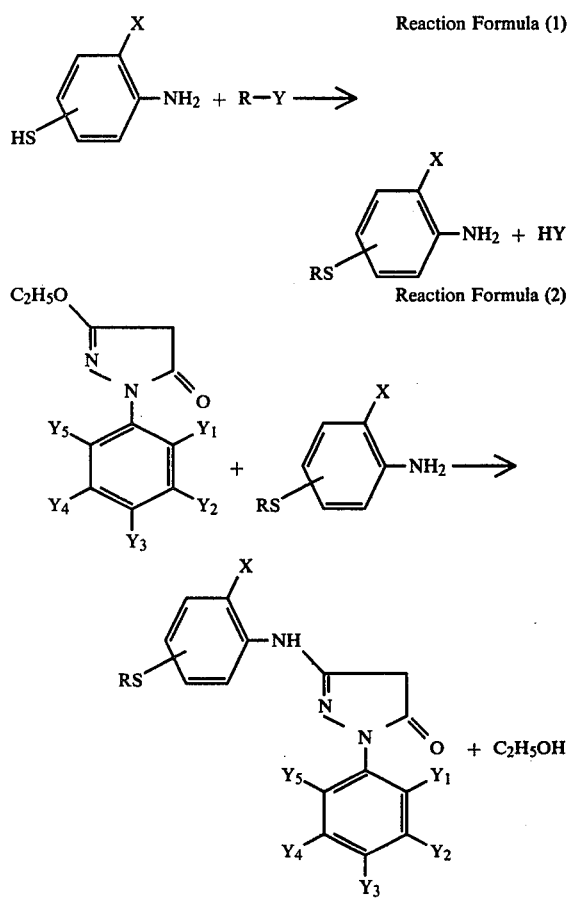

In the above formulae, X, R and a phenyl group substituted with $Y_1$, $Y_2$, $Y_3$, $Y_4$ and $Y_5$ each has the same meaning as defined hereinbefore and Y represents a halogen atom.

The anilino derivative which is one of the starting materials used in the reaction shown by the Reaction Formula (1) can be synthesized in an appropriate manner. For example, arylsulfonyl chloride can be reduced with zinc powder in the presence of concentrated sulfuric acid to obtain an arylmercaptan as described in *Organic Synthesis*, Coll. Vol. 1, 504 (1941); nitro-substituted benzenesulfonyl chloride can be reduced in the same condition as set forth above and, thereby, not only is sulfonyl chloride group but also the nitro group is reduced to obtain an amino-substituted thiophenol; and nitro-substituted benzenesulfonyl chloride can be reduced by metallic tin in the presence of concentrated hydrochloric acid as set forth in Synthesis Example 1 of the present invention. Details of the synthesis of the aniline derivative are shown in the Synthesis Examples given hereinafter. The substitution reaction shown in the Reaction Formula (1) can be carried out by reacting an anilino derivative with a compound of the formula R-Y (for example, alkyl halide, aryl halide and heterocyclic halide, etc., represented by R-Y are commercially available compounds. Further, when R is substituted, such compounds can be prepared easily by reference to typical organic chemistry text books.) in an amount of about 1 to about 10 times on a molar basis, preferably 1 to 2 times on a molar basis, based on the molar amount of the anilino derivative in the presence of a hydrogen halide removing agent in an amount of about 1 to about 10 times on a molar basis, preferably 1 to 2 times on a molar basis, based on the molar amount of the anilino derivative and a solvent at a reaction temperature of about 10° C. to about 100° C. Suitable examples of the hydrogen halide removing agents include a base, such as sodium hydroxide, potassium hydroxide, triethylamine, an alkoxide of an alkali metal, etc. Suitable examples of the solvent include an alcohol, an organic carboxylic acid solvent (such as acetic acid), a halogenated hydrocarbon solvent (such as chloroform), an aprotic polar solvent (such as dimethylformamide), etc.

The coupler-forming reaction shown in the Reaction Formula (2) can be carried out using the method described in U.S. Pat. No. 3,615,506, that is, by heating at about 50° to 200° C., preferably 100° to 150° C., 3-ethoxy pyrazolone and aniline derivative in an amount of 1 to 2 times based on the 3-ethoxypyrazolone in the presence of a catalytic amount (0.01 to 0.5 equivalent) of an acid (such as acetic acid, methanesulfonic acid, p-toluenesulfonic acid, etc.). The reaction can be carried out without a solvent or using solvent such as a hydrocarbon type solvent (for example, toluene, xylene), halogenized solvent (for example, ethylene chloride, methyl chloroform) and carboxylic acid type solvent (for example, formic acid, acetic acid, propionic acid, etc.). The carboxylic acid type solvent is preferred.

Typical synthesis examples for representative compounds of the invention are illustrated below. Unless otherwise indicated, all parts, percents, ratios and the like are by weight.

SYNTHESIS EXAMPLE 1

Synthesis of
1-(2,4,6-Trichlorophenyl)-3-(2-chloro-5-tetradecylthioanilino)-5-pyrazolone [Coupler (1)]

(1) Synthesis of 2-Chloro-5-mercaptoaniline

To a mixture of 100 g of chipped ice and 120 g of concentrated hydrochloric acid (35%), 120 g of metallic tin was added and then 25.4 g of 3-nitro-4-chlorobenzenesulfonyl chloride was added thereto. The mixture was stirred for one and a half hours while maintaining the temperature at 0° C. Then, the temperature was increased to 80° C. to 90° C. and the mixture was stirred with heating at the same temperature for 2 hours. After the completion of the reaction, the reaction solution was kept for one day in a cold place (at about −5° C. to about 10° C.). The crystals formed were collected and thoroughly washed with water. From the water used for the washing and the filtrate, newly formed crystals were also recovered and were added to the first crystals obtained.

Yield: 18 g, Melting Point: 140° to 170° C.

(2) Synthesis of 2-Chloro-5-tetradecylthioaniline 6.5 g of the mercapto intermediate, obtained as described in Step (1) above, was dissolved in 100 ml of methanol and, to this solution, an alkaline solution containing 3.6 g of potassium hydroxide dissolved in 20 ml of methanol was dropwise added. After stirring this mixture at room temperature (at about 20° C. to about 30° C. for 30 minutes, 9 g of tetradecylbromide was added and the mixture resulting was stirred at room temperature for 1 hour. To the mixture, 300 ml of ethyl acetate and excess amount of water were added and an extraction procedure was conducted. The ethyl acetate layer was thoroughly washed three times with water and dried over anhydrous sodium sulfate. The solvent was distilled off under reduced pressure. The residue was crystallized with hexane to obtain 9.3 g of white crystals having a melting point of 60.5° to 61.5° C.

(3) Synthesis of Coupler (1)

6.15 g of 1-(2,4,6-trichlorophenyl)-3-ethoxy-5-pyrazolone and 7.1 g of the aniline derivative obtained as described in Step (2) above were mixed. To the mixture, 0.5 ml of methanesulfonic acid was added and the mixture was heated at 120° to 140° C. with stirring. The organic compounds were dissolved at this temperature. After stirring for 1 hour, 0.5 ml of methanesulfonic acid was further added and the same temperature was maintained for 1 hour with stirring. When the amount of the desired compound had reached a maximum value, the reaction was interrupted and 50 ml of ethyl acetate was added to the reaction mixture. After removing colorless insoluble material by filtration, the ethyl acetate was distilled off under reduced pressure. The residue was crystallized with a solvent mixture of acetonitrile and ethyl acetate (5:1 by volume) to obtain 3.5 g of colorless crystals of the desired compound having a melting point of 64° to 66° C.

Elemental Analysis ($C_{29}H_{37}N_3SOCl_4$): Calculated (%): C: 56.40 H: 6.06 N: 6.80: Found (%): C: 56.60 H: 6.14 N: 6.86.

SYNTHESIS EXAMPLE 2

Synthesis of
1-(2,4,6-Trichlorophenyl)-3-(2-chloro-5-octadecylthioanilino)-5-pyrazolone [Coupler (10)]

17 g of 2-chloro-3-octadecylthioaniline (synthesized using the synthesis method as described in Step (1) and Step (2) of Synthesis Example 1) and 12 g of 1-(2,4,6-trichlorophenyl)-3-ethoxy-5-oxo-2-pyrazoline were mixed and the mixture was melted by heating at 130° to 140° C. To the melted product, 2 ml of methanesulfonic acid was added and the mixture was heated at the same temperature with stirring under reduced pressure for 4 hours. The same procedures as described in Synthesis Example 1 were repeated to obtain 11 g of Coupler (10) having a melting point of 78° to 79° C.

Elemental Analysis ($C_{33}H_{45}N_3SOCl_4$): Calculated (%): C: 58.83 H: 6.73 N: 6.23: Found (%): C: 58.81 H: 6.66 N: 6.07.

The magenta color-forming coupler in accordance with the present invention possesses both high coupling activity and sufficient solubility in an organic solvent, and, therefore, a color photographic element prepared using this coupler provides photographic properties such as a good sensitivity, gradation and the like, and possesses the characteristic that the photographic element is easy to prepare. Moreover, the color photographic element has the characteristics that not only does the photographic color image obtained by the development processing thereof possess a spectral absorption characteristic which is effective for color reproduction and sufficient light fastness, but also, after color development processing, yellow stain is reduced at the unexposed portions and increase in the yellow stain is minimal even on exposure to light for a long period of time, and, further, fading of the photographic color images due to light is markedly reduced.

Furthermore, the magenta color image obtained from the coupler in accordance with the present invention is resistant to the actions of heat and humidity. That is, the degree of color fading due to heat is serious with color images formed from 5-pyrazolones having an acylamino group or a ureido group at the 3-position thereof. This is believed to be due to the fact that the dyes formed react with the remaining coupler to produce a colorless product. For preventing color fading, a processing using a stabilizing solution containing formaldehyde or the like has been practiced, in general. A characteristic of the coupler of the present invention is that sufficient fastness without any such processing being necessary is obtained.

In order to prepare a silver halide color photographic light-sensitive element using the coupler of the present invention, one coupler of the present invention can be used individually, or two or more couplers of the present invention can be used as a mixture thereof, or the coupler of the present invention can also be used in combination with known magenta color image-forming couplers. Further, in order to enhance the color reproduction of color photographic light-sensitive elements, the magenta coupler of the present invention can also be used in the same emulsion layer in combination with a cyan or yellow coupler which has a different hue, e.g., as described in Japanese Patent Publication No. 391/1965.

Known open chain ketomethylene couplers can be used as yellow color-forming couplers in a photographic emulsion layer of the color photographic light-sensitive element according to the present invention. Of these couplers, benzoylacetanilide compounds and pivaloylacetanilide compounds are advantageous. Specific examples of suitable yellow color-forming couplers which can be used are described in U.S. Pat. Nos. 2,875,057, 3,265,506, 3,408,194, 3,551,155, 3,582,322, 3,725,072, 3,891,445, West German Patent No. 1,547,868, West German Patent Application (OLS) Nos. 2,213,461, 2,219,917, 2,261,361, 2,263,875, 2,414,006, etc.

Phenolic compounds, naphtholic compounds, etc., can be used as cyan color-forming couplers. Specific examples thereof which are suitable are described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411, West German Patent Application (OLS) Nos. 2,414,830, 2,454,329, Japanese Patent Application (OPI) No. 59,838/73.

Those colored couplers as described in, e.g., U.S. Pat. Nos. 3,476,560, 2,521,908, 3,034,892, Japanese Patent Publication Nos. 2,016/69, 22,335/63, 11,304/67, 32,461/69, Japanese Patent Application Nos. 98,469/74, 118,029/75, West German Patent Application (OLS) Nos. 2,418,959, etc., can also be used.

Those DIR couplers are described in, e.g., U.S. Pat. Nos. 3,227,554, 3,617,291, 3,701,783, 3,790,384, 3,632,345, West German Patent Application (OLS) Nos. 2,414,006, 2,454,301, 2,454,329, British Pat. No. 953,454, Japanese Patent Application No. 146,570/75, etc., can also be used.

The light-sensitive material of the present invention may also contain a compound capable of releasing a development inhibitor upon development other than a DIR coupler, for example, those compounds which are described in U.S. Pat. Nos. 3,297,445, 3,379,529, West German Patent Application (OLS) No. 2,417,914, etc., can be used.

Two or more of the above-described couplers may be incorporated in the same layer, or the same coupler may be incorporated in two or more different layers, if desired.

Known processes such as that described in U.S. Pat. No. 2,322,027 are suitable to incorporate the couplers into a silver halide emulsion layer. For example, a coupler is dissolved in an organic solvent having a high boiling point (180° C. or more) such as an alkyl phthalate (e.g., dibutyl phthalate, dioctyl phthalate, etc.), a phosphoric acid ester (e.g., diphenyl phosphate, triphenyl phosphate, tricresyl phosphate, dioctylbutyl phosphate, etc.), a citric acid ester (e.g., tributyl acetylcitrate, etc.), a benzoic acid ester (e.g., octyl benzoate, etc.), an alkylamide (e.g., diethyllaurylamide, etc.), or an organic solvent having a boiling point of about 30° to 150° C. such as a lower alkyl acetate (e.g., ethyl acetate, butyl acetate, etc.), ethyl propionate, sec-butyl alcohol, methyl isobutyl ketone, $\beta$-ethoxyethyl acetate, methyl Cellosolve acetate and then the solution is dispersed in a hydrophilic colloid. The above-described organic solvents having a high boiling point and the above-described organic solvents having a low boiling point may be mixed and used, if desired.

When couplers have an acid group such as a carboxylic acid group, a sulfonic acid group, etc., they can be incorporated in a hydrophilic colloid as an alkaline aqueous solution thereof.

The couplers including the magenta color-forming coupler of the present invention are generally used in an amount of $2 \times 10^{-3}$ to $5 \times 10^{-1}$ mol, preferably $1 \times 10^{-2}$ to $5 \times 10^{-1}$ mol, per mol of silver in the silver halide emulsion layer.

The photographic emulsion containing the coupler of the present invention can be coated onto conventional photographic supports such as film bases, baryta papers, resin coated papers or the like, and a variety of color light-sensitive elements such as a color positive film, a color negative film, a color reversal film, a color printing paper, etc., can thus be prepared.

Silver halides such as silver chloride, silver bromide, silver iodide, silver chlorobromide, silver chloroiodide, silver chlorobromoiodide or the like can be used in the photographic emulsion. These photographic emulsions can, if desired, contain the natural sensitizing agents which are present in gelatin, sulfur sensitizing agents, noble metal salts as well as reduction sensitizing agents. Further, optical sensitizing agents can also be incorporated in the photographic emulsion in order to impart an appropriate color sensitivity thereto. Conventional photographic additives, such as an anti-foggant, a stabilizer, an irradiation preventing dye, a coating aid, a polymer, a gelatin plasticizer, a hardening agent and the like can optionally be incorporated therein.

p-Substituted phenol derivatives are advantageously present in the color photographic light-sensitive element in accordance with the present invention, together with the coupler of the present invention, in order to improve the stabilities of color photographs prepared therefrom. Specific examples of p-substituted phenol derivatives which are particularly suitable for the color photographic light-sensitive element of the present invention include hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028; gallic acid derivatives as described in U.S. Pat. Nos. 3,457,079 and 3,069,262, and Japanese Patent Publication No. 13496/68; p-alkoxyphenols as described in U.S. Pat. No. 2,735,765 and Japanese Patent Application (OPI) No. 4738/72; p-oxyphenol derivatives such as chroman derivatives, spirochroman derivatives and tocopherol derivatives as described in U.S. Pat. Nos. 3,432,300, 3,573,050, and 3,574,627, as well as Japanese Patent Publication No. 20977/74, Japanese Patent Application (OPI) Nos.

35633/77, 147434/77 and 152225/77; 2,2'-methylene bisphenol derivatives as described in U.S. Pat. No. 3,700,455; p-alkylphenol derivatives as described in U.S. Pat. No. 3,700,455; and the like.

The hydrophilic colloid layers containing the coupler of the present invention, particularly a gelatin layer, can be hardened using a variety of cross-linking agents. In most cases, for example, inorganic compounds, such as a chromium salt or a zirconium salt, mucochloric acid or aldehyde type cross-linking agents, such as 2-phenoxy-3-chloromaleic aldehyde as described in Japanese Patent Publication No. 1872/71 can be advantageously employed in the present invention. Non-aldehyde type cross-linking agents such as polyepoxy compounds described in Japanese Patent Publication No. 7133/59, poly-(1-aziridinylated) compounds as described in Japanese Patent Publication No. 8790/62, as well as active halogen compounds as described in U.S. Pat. Nos. 3,362,827 and 3,325,287 are particularly useful for hardening.

The color photographic light-sensitive element containing the coupler of the present invention can be processed using conventional processing methods. That is, after image-wise exposure to light, the color photographic light-sensitive element is developed with a developer containing a p-phenylenediamine type developing agent and thereafter bleached and fixed. Thus, a color image having excellent spectral absorption characteristics and transparency is formed.

Typical examples of developing agents which are suitable for development of the color light-sensitive element in accordance with the present invention include 4-(N,N-diethylamino)aniline, 4-(N-ethyl-N-β-methanesulfonamidoethyl)-amino-2-methylaniline, 4-(N-ethyl-N-β-hydroxyethyl)amino-2-methylaniline, 4-N,N-diethylamino-2-methylaniline, etc.

Good results can be obtained with the color photographic light-sensitive element containing the coupler of the present invention by applying color development processing thereto, for example, a method which comprises halogenation-bleaching the developed silver formed by color development and color developing again to thereby increase the amount of dye formed as described in U.S. Pat. Nos. 2,439,901, 2,634,822, 2,814,565, 3,372,028 and the like, as described in U.S. Pat. Nos. 2,439,901, 2,623,822, 2,814,565, 3,372,028 and the like, or a method which comprises decreasing the amount of silver halide present in the light-sensitive element using a color intensifying method as described in U.S. Pat. No. 3,674,490, Japanese Patent Application (OPI) No. 9728/73, Japanese Patent Application No. 128327/74 or the like.

The photographic light-sensitive element which is employed in the present invention can also contain, as desired, an intermediate layer, an antihalation layer, a protective layer, a yellow filter layer, a backing layer, a mordant polymer layer, a developer-stain preventing layer and the like coated onto a support (including the back surface thereof) in addition to the silver halide emulsion layers. Silver halide emulsion layers for color photography include a red-sensitive silver halide emulsion layer, a green-sensitive silver halide emulsion layer and a blue-sensitive silver halide emulsion layer. The order of these layers is not limited and each of the respective layers can be separated into two or more layers for use.

The characteristics obtained in employing the magenta coupler of the present invention are more specifically explained below by reference to some specific examples. For Comparison, the magenta couplers indicated below, which are structurally similar to the magenta coupler of the present invention, were used.

Comparison Coupler (A)

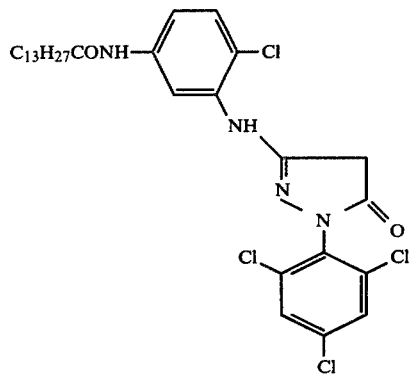

Comparison Coupler (B)

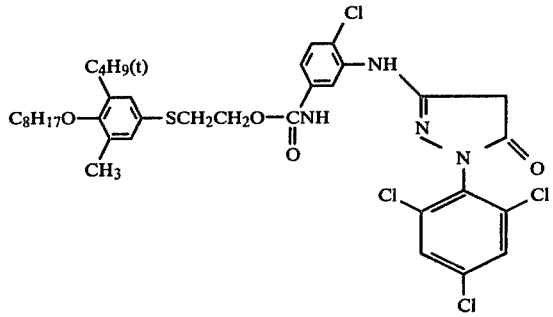

Comparison Coupler (C)

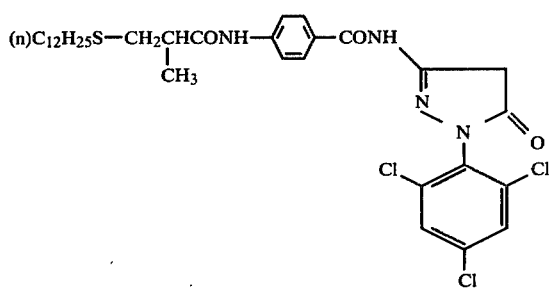

Comparison Coupler (D)

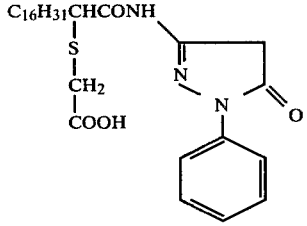

Comparison Coupler (E)

-continued

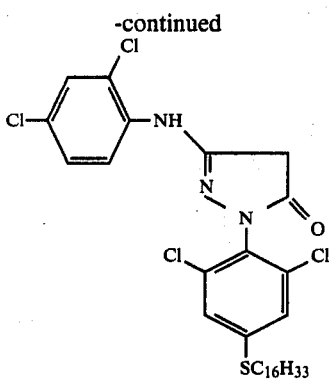

With Comparison Couplers (A), (B), (C), (D) and (E) indicated above and with Couplers (1) and (30) of the present invention, the spectral absorption characteristics of the azomethine dye formed by the oxidation coupling reaction with 4-[N-ethyl-N-($\beta$-methanesulfonamidoethyl)]amino-2-methylaniline were measured in ethyl acetate and compared.

From the spectral absorption curves obtained, the color density of the main wavelength was adjusted to 1.00 and the density of a second absorption appearing in the blue light region, the density at a longer wavelength of 60 m$\mu$ from the main wavelength and the width of the wavelength at which the color density became 0.50 were determined. The results obtained are shown in Table 1 below.

TABLE 1

| | Peak of Main Wave-Length (nm) | Color Density of Second Absorption | Color Density at 60 m Longer Wavelength | Width of Wavelength Having Density of 0.5 (nm) |
|---|---|---|---|---|
| Coupler (1) | 528 | 0.123 | 0.128 | 68 |
| Coupler (30) | 528 | 0.126 | 0.126 | 67 |
| Comparison Coupler (A) | 529 | 0.141 | 0.134 | 67 |
| Comparison Coupler (B) | 529 | 0.140 | 0.133 | 68 |
| Comparison Coupler (C) | 530 | 0.158 | 0.165 | 75 |
| Comparison Coupler (D) | 525 | 0.205 | 0.170 | 80 |
| Comparison Coupler (E) | 531 | 0.139 | 0.130 | 68 |

The color image obtained using the coupler of the present invention is sharply cut off at the long wavelength side and undesired second absorption is minimal. Further, the position of the main wavelength is appropriate, which are preferred for color reproduction. While not desiring to be bound, this is believed to be because the coupler of the present invention possesses a chlorine atom at the 2-position of and a sulfide bond at the 4- or 5-position of the anilino ring thereof.

The characteristics obtained using the magenta coupler of the present invention are explained further by reference to the examples hereinbelow.

EXAMPLE 1

A solution obtained by dissolving 3.7 g of Coupler (1) of the present invention, 4.0 ml of tricresyl phosphate and 12 ml of ethyl acetate with heating at 60° C. was added to 40 ml of an aqueous solution containing 4 g of gelatin, 0.10 g of sodium dodecylbenzenesulfonate at 60° C. The solution mixture was stirred with a homogenizer to prepare a coupler dispersion. The coupler dispersion was mixed with 100 g of a green-sensitive photographic emulsion containing $4.70 \times 10^{-2}$ mol of silver chlorobromide (50 mol% silver chloride) and 9 g of gelatin, and 5 ml of a 3% acetone solution of triethylenephosphoramide was further added thereto as a hardening agent. After adjusting the pH to 7.0, the dispersion was coated onto a paper sheet having polyethylene coated thereon in a thickness of 3.4 microns (dry thickness; hereafter all thicknesses given are dry thicknesses). Gelatin was coated thereon (using a 2% gelatin aqueous solution) in a thickness of 1 micron to prepare a color print paper (Sample (H)).

Color print papers were prepared in a manner similar to the preparation of Sample (H) except that Couplers (16) and (30) were employed in lieu of Coupler (1) and Comparison Couplers (A), (B), (C) and (E) were employed as magenta color image-forming couplers for comparison, respectively. Samples (I) and (J) were prepared from Couplers (16) and (30), and Samples (K), (L), (M) and (N) were prepared from Comparison Couplers (A), (B), (C) and (E), respectively.

These samples were exposed to green light using a step wedge and processed in the following development processings.

| Processing Step | Temperature | Time |
|---|---|---|
| 1. Color Development | 30° C. | 4 min |
| 2. Bleach-Fixing | " | 2 min |
| 3. Water Washing | " | 2 min |
| 4. Stabilizing | " | 2 min |

The processing solutions used had the following compositions:

| Composition of Color Developer | | |
|---|---|---|
| Sodium Metaborate | 25 | g |
| Sodium Sulfite | 2 | g |
| Hydroxylamine (sulfate) | 2 | g |
| Potassium Bromide | 0.5 | g |
| 6-Nitrobenzimidazole (nitrate) | 0.02 | g |
| Sodium Hydroxide | 4 | g |
| Benzyl Alcohol | 15.8 | ml |
| Diethylene Glycol | 20 | ml |
| 4-(N-Ethyl-N-$\beta$-methanesulfonamidoethyl)-amino-2-methylaniline Sesquisulfate | 8 | g |
| Water to make | 1 | l |
| Composition of Bleach-Fixing Solution | | |
| Ferric Salt of Ethyelnediamine-tetraacetate | 45 | g |
| Ammonium Thiocyanate | 10 | g |
| Sodium Sulfite | 10 | g |
| Ammonium Thiosulfate (60% aq. soln.) | 100 | ml |
| Tetrasodium Ethyelnediaminetetraacetate | 5 | g |
| Water to make | 1 | l |
| Composition of Stabilizing Bath (a) | | |
| Tartaric Acid | 10 | g |
| Zinc Sulfate | 10 | g |
| Sodium Metaborate | 20 | g |
| Water to make | 1 | l |

With respect to the samples obtained, the yellow stain density at the unexposed area was determined by measuring the reflection density thereof with a densitometer equipped with a blue filter. Thereafter, these samples were stored for 2 weeks under a fluorescent light (about 28,000 lux) and the rate of increase in the yellow stain density was measured. The results obtained are shown in Table 2 below.

TABLE 2

| Sample No. | Coupler Used | Yellow Stain Density at Unexposed Area | |
|---|---|---|---|
| | | Initial Density | After Irradiation |
| (H) | Coupler (1) | 0.01 | 0.08 |
| (I) | Coupler (16) | 0.01 | 0.09 |
| (J) | Coupler (30) | ≦0.01 | 0.06 |
| (K) | Comparison Coupler (A) | 0.02 | 0.12 |
| (L) | Comparison Coupler (B) | 0.03 | 0.18 |
| (M) | Comparison Coupler (C) | 0.02 | 0.15 |
| (N) | Comparison Coupler (E) | 0.02 | 0.13 |

It is clear from the results shown in Table 2 above that the samples using the magenta couplers of the present invention had a reduced yellow stain density at the unexposed areas and less increase in yellow stain density upon irradiation with light.

EXAMPLE 2

Onto a paper sheet whose surface was covered with polyethylene were coated, as a first layer, a blue-sensitive silver chlorobromide emulsion (20 mol% chloride) containing α-pivaloyl-α-(5,5-dimethyl-3-hydantoinyl)-2-chloro-5-[α-(2,4-di-tert-amylphenoxy)-butyramido]acetanilide in a thickness of 3.0 microns, and thereon gelatin in a thickness of 1.5 microns as a second layer in a manner similar to Example 1.

A solution obtained by dissolving 3.7 g of Coupler (1) of the present invention, 0.3 g of 2,5-di-tert-octylhydroquinone, 0.4 g of 6,6'-dihydroxy-7,7'-dimethoxy-4,4,4',4'-tetramethylbis-2,2'-spirochroman, 4.0 ml of tricresyl phosphate and 12 ml of ethyl acetate with heating at 60° C. was added to 40 ml of an aqueous solution containing 4 g of gelatin and 0.10 g of sodium dodecylbenzenesulfonate at 60° C. The solution mixture was stirred with a homogenizer to prepare a coupler dispersion. The coupler dispersion was mixed with 100 g of a green-sensitive photographic emulsion containing $4.70 \times 10^{-2}$ mol of silver chlorobromide (50 mol% silver chloride) and 9 g of gelatin and 5 ml of a 3% acetone solution of triethylene phosphoramide was added thereto as a hardening agent. After adjusting the pH to 7.0, the dispersion was coated on the above-described second layer as a third layer in a thickness of 3.4 microns. Then, gelatin containing 2-(5-chlorobenzotriazol-2-yl)-4-methyl-6-tertbutylphenol and 2-(benzotriazol-2-yl)-4-tertbutylphenol was coated in a thickness of 1.5 microns as a fourth layer. A red-sensitive emulsion containing 2-[α-(2,4-di-tertamylphenoxy)-butyramido]-4,6-dichloro-5-methylphenol was coated in a thickness of 2.5 microns as a fifth layer, and finally as an uppermost layer, gelatin was coated in a thickness of 1 micron to prepare a color printing paper (Sample (O)).

Color printing papers were prepared in a manner similar to Sample (O) except that, in lieu of Coupler (1), Couplers (16) and (30) were further employed, as magenta color image-forming couplers, and Comparison Couplers (A), (B), (C), (D) and (E) were employed. However, the color printing paper using Comparison Coupler (D) was not a good color printing paper since the emulsion layer containing the coupler was not uniformly coated due to the low solubility of Comparison Coupler (D).

The samples obtained from Couplers (16) and (30) of the present invention were designated Samples (P) and (Q), and those from Comparison Couplers (A), (B), (C), (D) and (E), were designated Samples (R), (S), (T), (U) and (V), respectively.

These samples were exposed to green light using a step wedge and development processings similar to those described in Example 1 were performed. Development processing using a Stabilizing Bath (b) containing formaldehyde as described below in lieu of Stabilizing Bath (a) shown in Example 1 was also performed for Samples (O), (Q) and (T).

| Composition of Stabilizing Bath (b) | |
|---|---|
| Tartaric Acid | 10 g |
| Zinc Sulfate | 10 g |
| Sodium Metaborate | 20 g |
| Formaldehyde (40% aq. soln.) | 10 ml |
| Water to make | 1 l |

Each of the respective samples was subjected to the development processing described above. The thus-formed color images were stored for 2 weeks under a fluorescent light (about 28,000 lux) and the rate (%) of decrease in color density was measured at an initial magenta color image density of 1.0. The results obtained are shown in Table 3 below.

TABLE 3

Light Fastness of Color Image

| Sample No. | Coupler Employed | Stabilizing Bath | Rate of Decrease in Color Density (%) |
|---|---|---|---|
| (O) | Coupler (1) | (a) | 11 |
| (P) | Coupler (16) | (a) | 12 |
| (Q) | Coupler (30) | (a) | 8 |
| (R) | Comparison Coupler (A) | (a) | 21 |
| (S) | Comparison Coupler (B) | (a) | 45 |
| (T) | Comparison Coupler (C) | (a) | 35 |
| (U) | Comparison Coupler (D) | (a) | 55 |
| (V) | Comparison Coupler (E) | (a) | 19 |

Then, of these, Samples (O), (Q) and (T) were stored at 120° C. for 4 hours, and at 60° C. under 75% RH for 3 weeks, and the rate of decrease in color density to an initial color density of the magenta color images were measured. The results obtained are shown in Table 4 below.

TABLE 4

Fastness of Color Image to Heat and Humidity

| Sample No. | Coupler Employed | Stabilizing Bath | Rate of Decrease in Color Density (%) | | | |
|---|---|---|---|---|---|---|
| | | | 120° C. 4 Hours Initial Density | | 60° C., 75% RH 3 Weeks Initial Density | |
| | | | 0.5 | 1.0 | 0.5 | 1.0 |
| (O) | Coupler (1) | (a) | 6 | 4 | 10 | 9 |
| | | (b) | 6 | 4 | 9 | 9 |
| (Q) | Coupler (30) | (a) | 7 | 5 | 10 | 8 |
| | | (b) | 6 | 4 | 9 | 6 |
| (T) | Comparison Coupler (C) | (a) | 42 | 37 | 65 | 37 |
| | | (b) | 16 | 10 | 21 | 13 |

It can be seen from these results that the couplers of the present invention provide color images which are extremely fast to light, and also form color images which are sufficiently fast to heat and humidity without necessitating the use of a stabilizing bath containing formaldehyde.

Further, these samples were exposed to light through a transparent original having a color negative image thereon, and development processings were performed as above indicated to thereby obtain color prints. The red portion of the print obtained from Sample (O) in accordance with the present invention was less dark and was sharper in comparison with that of Sample (T) and Sample (U) containing the comparison couplers indicated above.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive element comprising a support having thereon a silver halide emulsion layer containing therein a 3-anilino-5-pyrazolone magenta color-forming coupler represented by the following general formula

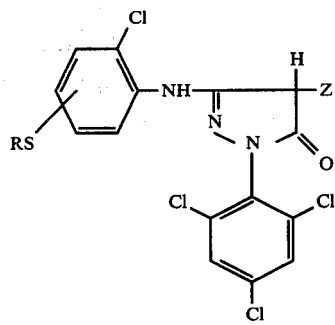

wherein R represents an aliphatic hydrocarbon group having up to about 35 carbon atoms, a heterocyclic group having up to 22 carbon atoms or an aromatic group having up to 22 carbon atoms; and Z represents a hydrogen atom or a group which is eliminated on coupling by the oxidation product of an aromatic primary amine developing agent; and the RS group is present at the 4- or 5-position of the anilino group.

2. The color photographic light-sensitive element as claimed in claim 1, wherein Z represents a hydrogen atom.

3. The color photographic light-sensitive element as claimed in claim 1, where Z represents a group which is eliminated on coupling by the oxidation product of an aromatic primary amine developing agent.

4. The color photographic light-sensitive element as claimed in claim 1, wherein R represents a straight chain or branched chain alkyl group having 1 to 22 carbon atoms, an aryl group having 6 to 22 carbon atoms or a heterocyclic group having 5 to 22 carbon atoms.

5. The color photographic light-sensitive element as claimed in claim 4, wherein Z represents a hydrogen atom, a thiocyano group, an acyloxy group, an aryloxy group, an alkoxy group, a halogen atom, an arylazo group, a benzotriazolyl group, a naphthotriazolyl group, an alkylthio group, an arylthio group, a heterocyclic thio group, an aralkoxycarbonyloxy group, an alkoxycarbonyloxy group, an aryloxycarbonyloxy group, a cycloalkylthio group, a cycloalkoxy group, an imido group, an imidazolyl group, a triazolyl group, an acylamino group, a sulfonamido group or a cycloamino group.

6. The color photographic light-sensitive element as claimed in claim 1, wherein said magenta color-forming coupler represented by the general formula in claim 1 is selected from the group consisting of

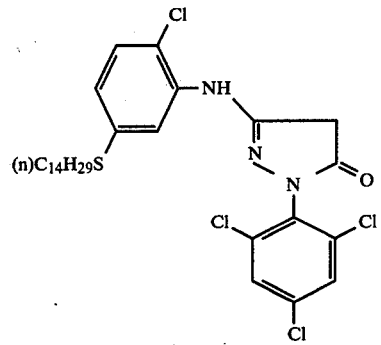

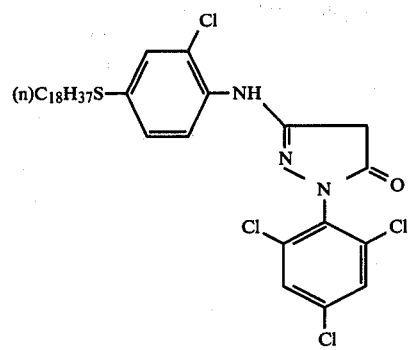

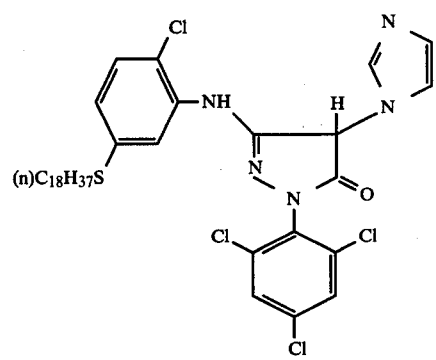

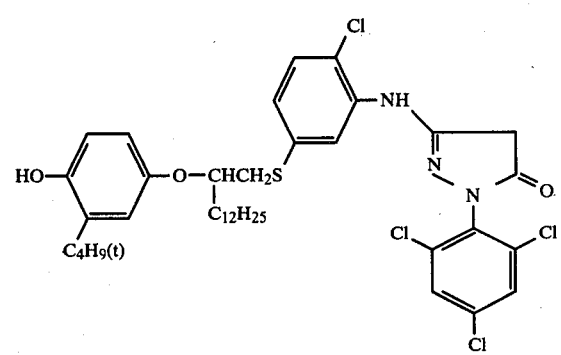

-continued
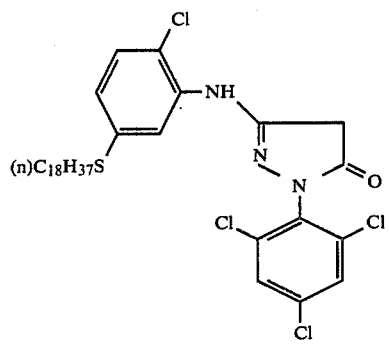
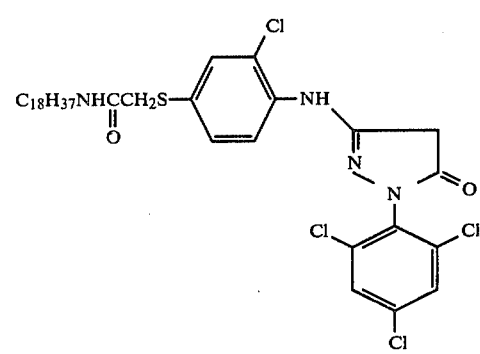
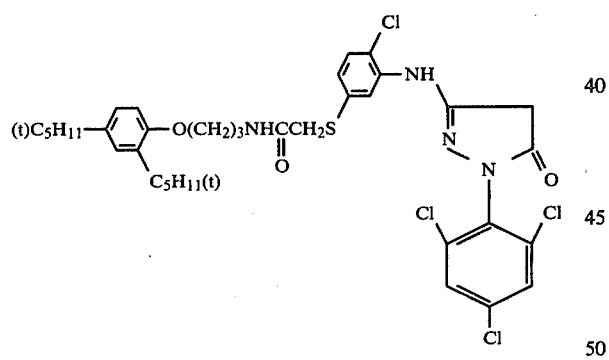
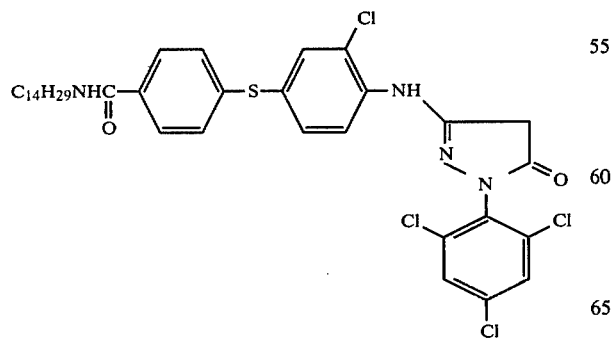
-continued
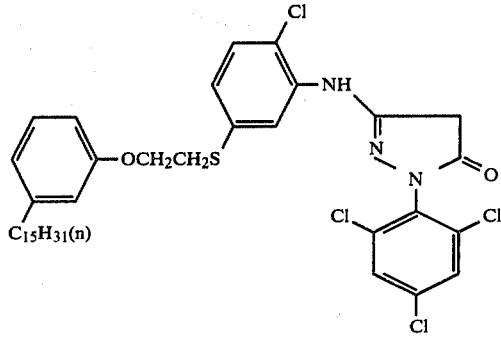
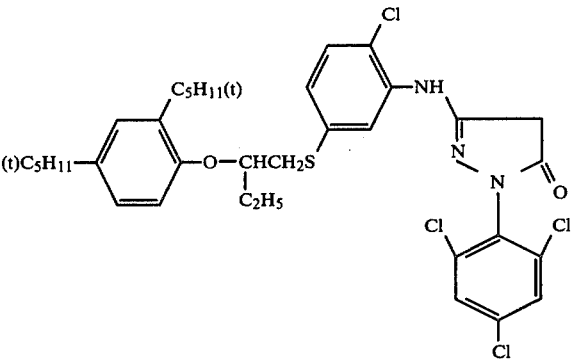
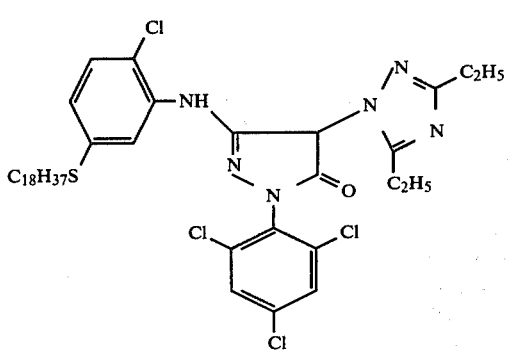
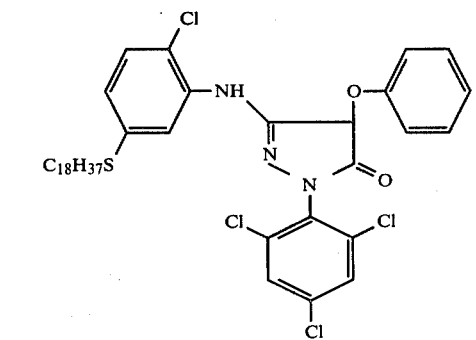

-continued

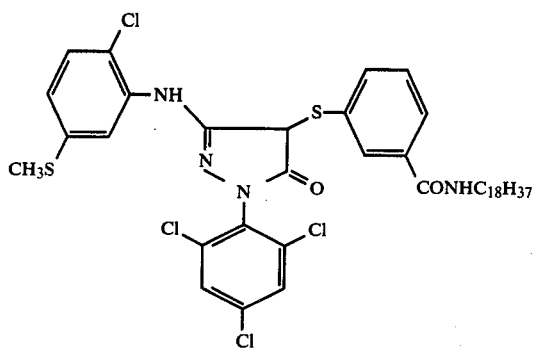

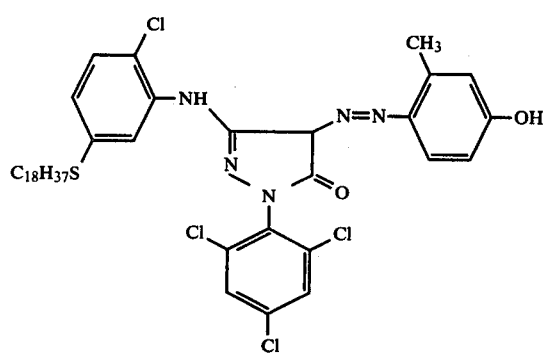

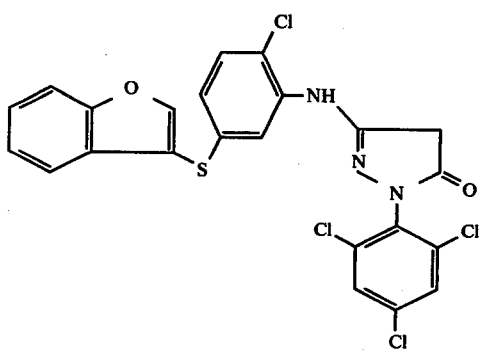

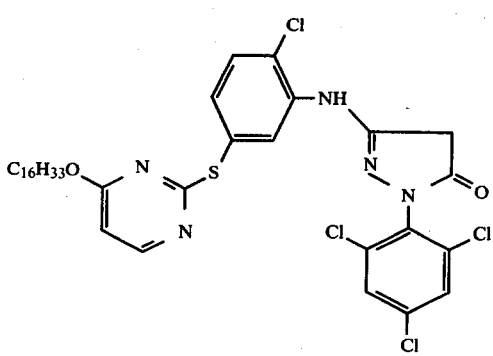

-continued

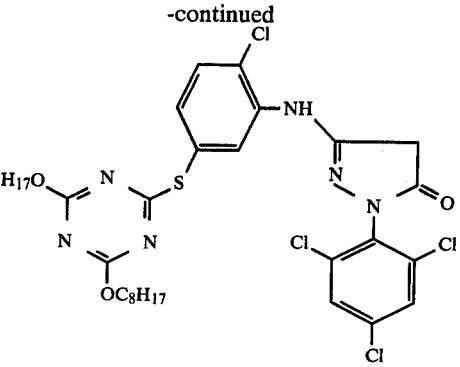

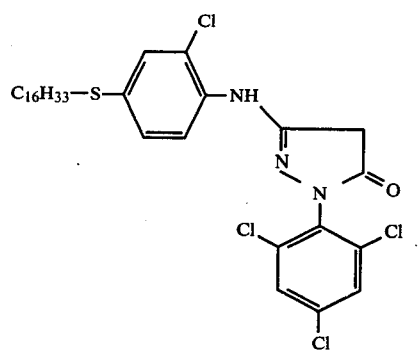

and

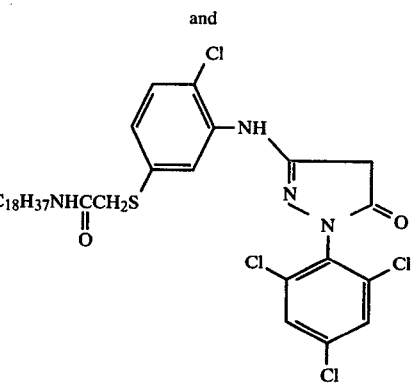

7. The color photographic light-sensitive element as claimed in claim 1, wherein said silver halide emulsion layer is a green-sensitive silver halide emulsion layer.

8. The color photographic light-sensitive element as claimed in claim 1, wherein said silver halide emulsion layer is a green-sensitive silver halide emulsion layer containing said magenta color-forming coupler represented by the general formula as set forth in claim 1, and said color photographic light-sensitive element further includes a red-sensitive silver halide emulsion layer and a blue-sensitive silver halide emulsion layer.

9. The color photographic light-sensitive element as claimed in claim 1, wherein said silver halide emulsion layer is a green-sensitive silver halide emulsion layer containing said magenta color-forming coupler represented by the general formula as set forth in claim 1, and said color photographic light-sensitive element additionally includes a red-sensitive silver halide emulsion layer containing a phenolic or naphtholic cyan color-forming coupler, and a blue-sensitive silver halide emulsion layer containing a benzoylacetanilide or pivaloylacetanilide yellow color-forming coupler.

10. The color photographic light-sensitive element as claimed in claim 1, wherein said silver halide emulsion layer contains a p-substituted phenol derivative.

11. The color photographic light-sensitive element as claimed in claim 10, wherein said p-substituted phenol derivative is a hydroquinone derivative, a gallic acid derivative, a p-alkoxyphenol, a chroman derivative, a spirochroman derivative, a tocopherol derivative, 2,2′-methylene bisphenol derivative, or a p-alkylphenol derivative.

* * * * *